(12) United States Patent
Sano et al.

(10) Patent No.: US 7,722,557 B2
(45) Date of Patent: May 25, 2010

(54) BLOOD PURIFICATION APPARATUS

(75) Inventors: Yoshihiko Sano, Osaka (JP); Makoto Mitsuhashi, Osaka (JP); Hidetoshi Saio, Osaka (JP)

(73) Assignee: Nipro Corporation, Osaka (JP)

( * ) Notice: Subject to any disclaimer, the term of this patent is extended or adjusted under 35 U.S.C. 154(b) by 295 days.

(21) Appl. No.: 11/266,284

(22) Filed: Nov. 4, 2005

(65) Prior Publication Data

US 2006/0100564 A1    May 11, 2006

(30) Foreign Application Priority Data

Nov. 5, 2004    (JP)    ............................. 2004-322498

(51) Int. Cl.
*A61M 37/00* (2006.01)
*C02F 1/44* (2006.01)

(52) U.S. Cl. .................... 604/6.09; 604/4.01; 604/5.01; 604/5.04; 604/6.1; 604/6.11; 210/645; 210/646; 210/739; 210/741

(58) Field of Classification Search .................. 210/645, 210/646, 739, 741, 195.2, 416.1, 433.1, 500.21; 422/44; 604/4.01, 5.01, 5.04, 6.09, 6.1, 6.11
See application file for complete search history.

(56) References Cited

U.S. PATENT DOCUMENTS

| 4,412,916 A | 11/1983 | Kell ............................ 210/90 |
| 4,606,826 A | 8/1986 | Sano et al. ................... 210/646 |
| 5,591,344 A | 1/1997 | Kenley et al. ............... 210/636 |
| 5,725,775 A * | 3/1998 | Bene et al. ................... 210/646 |

FOREIGN PATENT DOCUMENTS

| DE | 37 20 664 A1 | 1/1989 |
| EP | 0 143 341 A2 | 6/1985 |
| EP | 0 992 255 A2 | 4/2000 |
| EP | 1 213 035 A1 | 6/2002 |
| JP | 2002-233570 A | 8/2002 |
| WO | 2004/061399 A3 | 7/2004 |

* cited by examiner

*Primary Examiner*—Leslie R Deak
(74) *Attorney, Agent, or Firm*—Kubovcik & Kubovcik

(57) ABSTRACT

A blood purification apparatus in which the pressure in a circuit is measured by directly measuring the strain of an air trap by a strain sensor without providing a pressure measuring section in the circuit.

7 Claims, 11 Drawing Sheets

BLOOD PURIFICATION APPARATUS

FIELD OF THE INVENTION

The present invention relates to a blood purification apparatus for assisting or carrying out functions of internal organs of a living body by purifying blood drawn out from a blood vessel in the body, and adding an effective substance thereto if needed, and is characterized in that the internal pressure of a blood circuit can be measured by measuring the strain of a venous side air trap in the blood circuit by a strain sensor.

BACKGROUND OF THE INVENTION

In the related art, in blood purification therapy, measurement of the arterial pressure (also referred to as the filter inlet pressure) and the venous pressure during extracorporeal circulation is carried out with a pressure monitor line provided on an air trap chamber in an extracorporeal circuit connected to respective pressure sensors. In this method, the pressure is measured via air, and hence adjustment of a liquid level in the chamber is required when priming is completed or during the treatment in order to provide an air space. The adjustment of the liquid level is carried out by pushing and pulling a syringe, which is connected to a distal end of a liquid level adjustment line provided separately in the air trap chamber. However, this procedure requires a certain level of skill, and if the procedure is conducted improperly, blood may jet out and come into contact with a human body or a pressure sensor protecting filter, whereby a high risk of infection results.

Therefore, various blood pressure measurement devices including a pipe and at least one section for measuring the pressure of blood flowing in the pipe are proposed. These devices include a substantially hard wall and a hole sealed by a closing member which can be resiliently deformed or displaced, and the inner surface of the pipe comes into contact with blood and the outer surface thereof comes into contact with the outside air so that a force exerted on the closing member can be measured by a load sensor. For example, such blood pressure measurement devices include (1) a device in which an air compartment is provided between a thin film (or diaphragm) and a load sensor so as to measure directly the internal pressure in the air compartment which varies with displacement of the thin film, (2) a device in which a force exerted on the inner surface of a flexible thin film, which is provided for sealing a hole provided on a wall of the compartment, is transmitted to a load sensor via a load transmitter, to be measured, (3) the device in (2), in which a metallic disk is mounted to the outer surface of the flexible thin film, and a magnet is attached to the end of the shaft of a load transmitter, so that the flexible thin film is fixed to the load transmitter, and (4) a device in which a closing member is formed in a single member which includes a hard wall of a blood pressure measurement section. See JP-A-2002-233570 (FIG. 1, FIG. 2, FIG. 3, and FIG. 6).

However, the device in (1) described above has a drawback such that the seal of the air compartment may be broken during use, and when the seal is broken, the pressure transmitting function may be lost. The devices in (2) to (3) described above have a drawback in that the hole on the wall must be sealed completely with the thin film, and hence mounting of the thin film onto the wall of the compartment is relatively complicated, whereby manufacture and assembly of the devices are difficult. The device shown in (4) also has a drawback in that the section which can be resiliently deformed is formed to have a waveform outer shape, whereby manufacture and assembly of the device are also difficult. All of the devices (1) to (4) described above include an inner wall of a pressure measuring section, which is larger than the inner wall of a liquid circulation circuit, and whose shape is square in cross-section. Therefore, when it is applied to a blood circulation circuit, eddy flow occurs in blood flowing into the pressure measuring section, and hence there is a risk that plaque formation may result.

SUMMARY OF THE INVENTION

The present invention has been made to solve such circumstances, and has an object to provide a blood purification apparatus which can measure the pressure in a blood circuit by directly measuring strain of the venous-side air trap by a strain sensor without providing a pressure measuring section in the blood circuit.

A blood purification apparatus according to the present invention includes: a blood purifier and a blood circuit, a blood pump, a priming liquid feed line, a venous-side air trap, an opening-closing valve provided in the venous-side blood circuit on the downstream side of the venous-side air trap, a dialysate circuit, a dialysate pump, and a filtering pump, and is characterized in that a strain sensor is provided on the venous-side air trap so that the strain of the venous-side air trap is measured by the strain sensor thereby measuring the pressure in the venous-side blood circuit.

It is also possible to provide an air trap in an arterial-side blood circuit and to provide a strain sensor on the arterial-side air trap, so that the pressure in the arterial-side blood circuit can be measured by measuring the strain of the arterial-side air trap by the strain sensor. It is also possible to provide a replenisher feed line in the venous-side blood circuit. The strain sensor which is preferably employed includes a load sensor and a load transmitter, so that a force exerted onto the internal surface of the air trap is transmitted to the load sensor via the load transmitter to be measured thereby. The strain sensor may be accommodated in a housing which includes a groove for accommodating a body of the air trap and a load sensor compartment formed on the bottom of the groove, and the housing may include fixing means with respect to the air trap. A lid which can be locked with the housing may be employed as the fixing means.

Although the present invention has generally been described, further understanding may be achieved by making reference to several specific embodiments. These embodiments are provided in this specification only as examples, and are not intended to limit the invention unless otherwise specified.

THE MOST PREFERRED EMBODIMENTS OF THE INVENTION

A venous-side air trap and an arterial-side air trap are provided with strains sensors, respectively, so that the strains of the air traps can be measured by these strain sensors. A replenisher feed line is provided in a venous-side blood circuit.

First Embodiment

Figure 1:
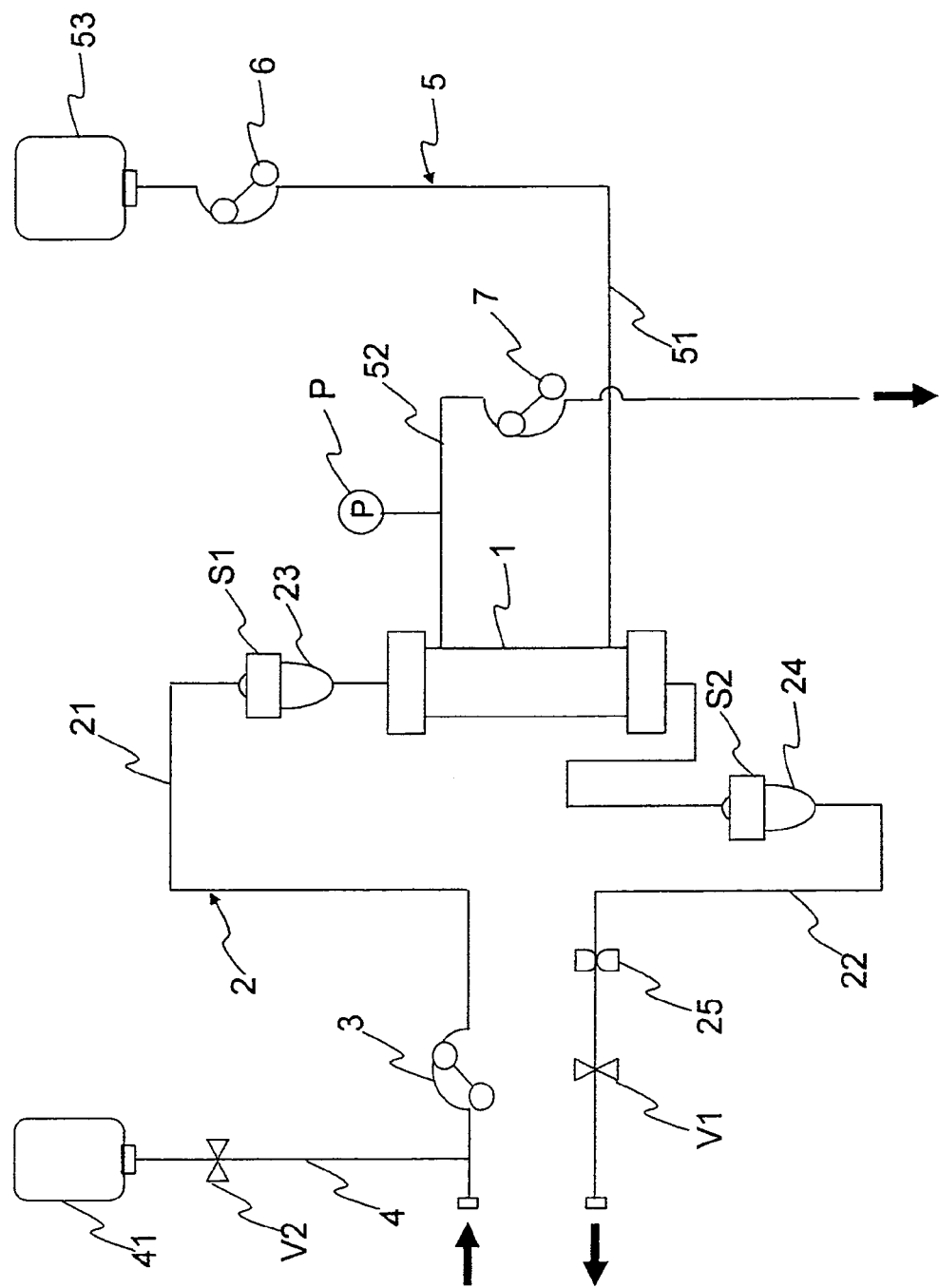
FIG. 1 is a schematic diagram showing a blood purification apparatus according to a first embodiment of the present invention.

Referring now to FIG. 1, a first embodiment will be described.

FIG. 1 is a schematic diagram of a blood purification apparatus according to a first embodiment.

The blood purification apparatus of the first embodiment is a blood purification apparatus for conducting a continuous venovenous hemodialysis (CVVHD). As shown in FIG. 1, it includes a blood purifier 1 and a blood circuit 2 (21, 22), a blood pump 3, a priming liquid feed line 4, an arterial-side air trap 23, a venous-side air trap 24, an opening-closing valve V1, a dialysate circuit 5 (51, 52), a dialysate pump 6, and a filtering pump 7. The arterial-side air trap 23 and the venous-side air trap 24 are provided with strain sensors S1, S2, respectively, so that the pressure in the arterial-side circuit and the venous-side circuit can be measured by measuring the strain of the air trap by the strain sensors S1, S2.

The blood circuit 2 includes an arterial-side blood circuit 21 on the upstream side of the blood purifier 1 and a venous-side blood circuit 22 on the downstream side of the blood purifier 1. The arterial-side blood circuit 21 has the priming liquid feed line 4 connected thereto on the upstream side of the blood pump 3 (there may be a case where the priming liquid feed line 4 is provided on the downstream side of the blood pump 3), and the air trap (chamber) 23 for separating air in blood is provided on the downstream side of the blood pump 3 in the vicinity of the blood purifier 1. In the case of normal hemodialysis, different from CVVHD, in which hemodialysis is conducted continuously for a long time, the arterial-side air trap 23 may be omitted. The strain sensor S1 is provided on the air trap 23. The air trap 24 is provided in the venous-side blood circuit 22 at a position close to the blood purifier 1, and an air bubble sensor 25 and the opening-closing valve V1 are provided on the downstream side of the air trap 24 in this order. The strain sensor S2 is provided on the air trap 24. The priming liquid feed line 4 is, when provided on the upstream side of the blood pump 3, adapted to feed priming liquid from a priming liquid container 41 to the blood circulation circuit (including the arterial-side blood circuit 21, the blood purifier 1, and the venous-side blood circuit 22) by driving of the blood pump 3 when an opening-closing valve V2 is opened.

The dialysate circuit 5 includes a dialysate feed circuit 51 on the upstream side of the blood purifier 1 and a drainage circuit 52 on the downstream side of the blood purifier 1. A dialysate container 53 is connected to the dialysate feed circuit 51, so that a dialysate is fed from the dialysate container 53 to the blood purifier 1 by driving of the dialysate pump 6. Generally, a pressure gauge P and the filtering pump 7 are provided in the drainage circuit 52 in this order, so that used dialysate is drained from the blood purifier 1 by the driving of the filtering pump 7. It is also possible to connect the dialysate feed circuit 51 and the drainage circuit 52 to an ultrafiltration amount control device (including the filtering pump) instead of connecting the drainage circuit 52 to the filtering pump 7. The pressure gauge P may be of any type as long as it has been used in blood purification apparatus in the related art. The location of installation of the pressure gauge P is preferably on the drainage circuit 52 side as shown in FIG. 1, but may be on the dialysate feed circuit 51 side as long as it is in the dialysate circuit 5 between the dialysate pump 6 and the filtering pump 7.

The strain sensor S includes a housing 91 having a groove 911 which is capable of accommodating an air trap C, a lid member 92 for fixing the housing 91 to the air trap C, a load sensor 93 provided in the groove 911 of the housing 91, and a load transmitter 94 as shown in FIG. 4 to FIG. 7. A force exerted on the inner surface of the air trap C is transmitted to the load sensor 93 via the load transmitter 94 to be measured thereby. The housing 91 is provided with the groove 911 which can accommodate the air trap C, and a load sensor compartment 912 for locating the load sensor 93, and the load sensor 93 is accommodated in the load sensor compartment 912 and fixed therein. The load sensor 93 includes the load transmitter 94 mounted thereto, so that when the air trap C is accommodated in the groove 911, the distal end of a head 941 of the load transmitter 94 comes into hermetical contact with the outer wall of a body portion of the air trap C, whereby the body portion is compressed by an adequate force. The lid member 92 has a function to protect the air trap C from the influence of atmospheric temperature, and is provided with a recessed groove 921 on the inner wall thereof so as to come just into hermetical contact with the air trap C when the lid is closed. As means for fixing the housing 91 to the air trap C, various fixing means other than the lid member 92 may be employed, for example, a hook having an arm-shaped arm, a rubber band, or a structure which enables the pressure measuring section to be fitted into the groove (a structure in which an opening of the groove is narrowed, and adapted to be resiliently extended when being fitted), although not shown.

The load sensor 93 which is generally employed is of a strain gauge type, although it is not limited. In the drawings (see, in particular, FIG. 7), reference numeral 95 designates a lead, reference numeral 913 designates a hook for fixing the lid member 92 to the housing 91, and reference numeral 922 designates an engaging portion with respect to the hook.

Second Embodiment

Figure 2:
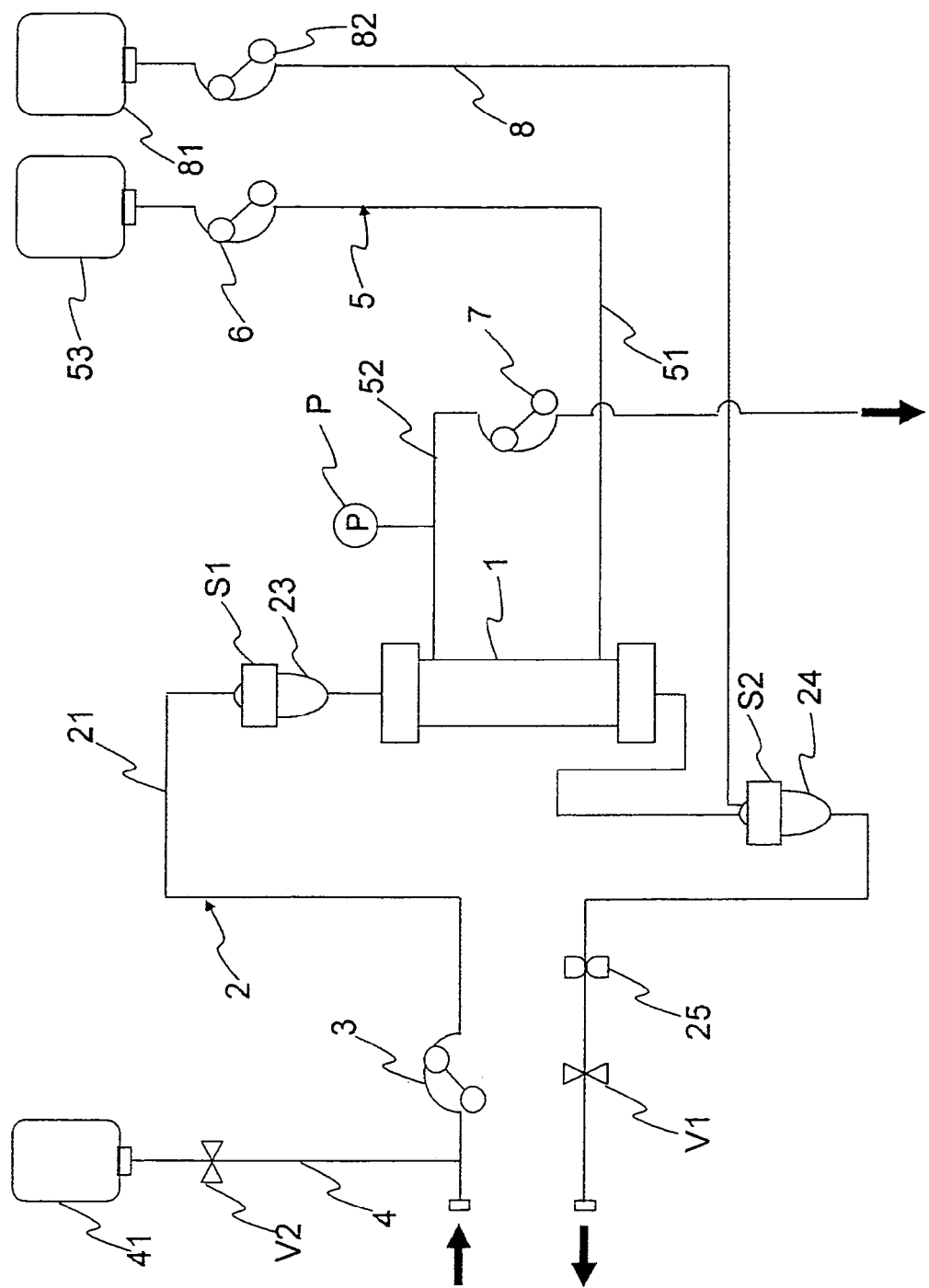
FIG. 2 is a schematic diagram showing a blood purification apparatus according to a second embodiment of the present invention.
Figure 3:
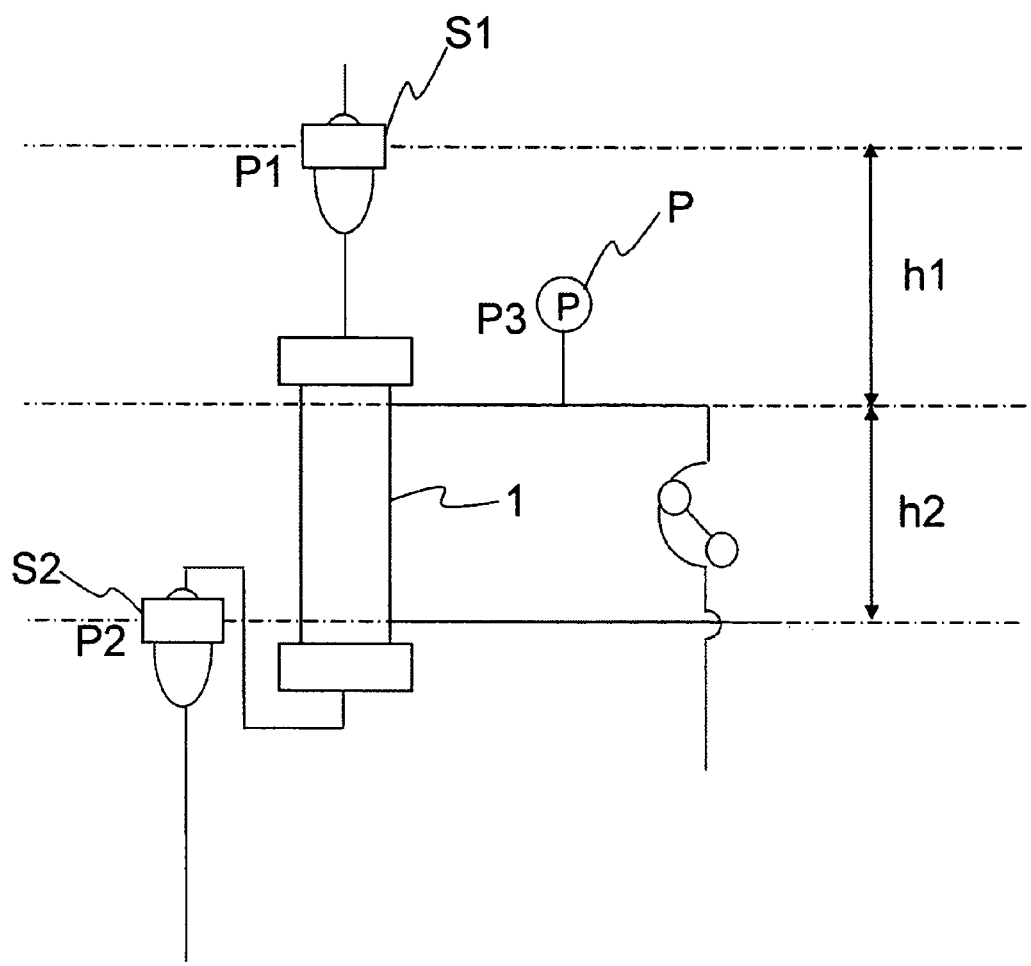
FIG. 3 is a diagram showing the relation among the pressure measured by a strain sensor, the head between the position of the strain sensor and a pressure gauge P, and the pressure measured by the pressure gauge P.
Figure 4:
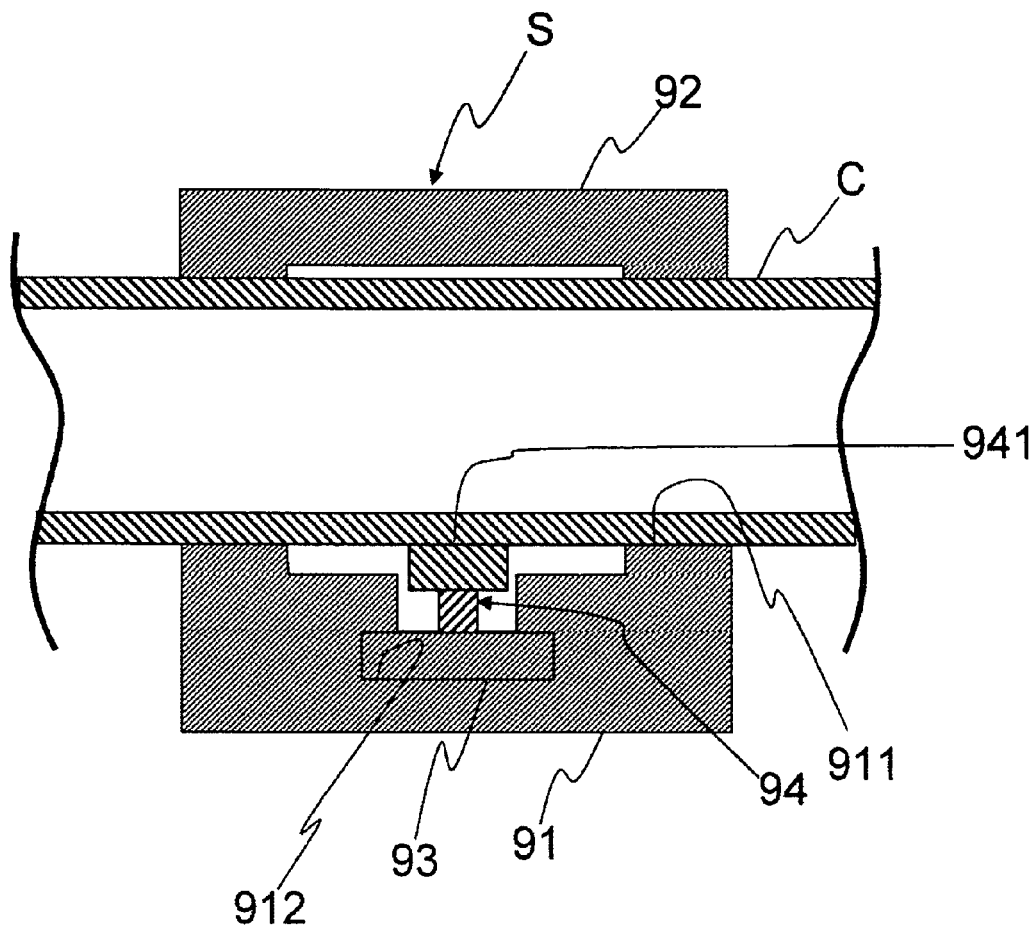
FIG. 4 is a vertical cross-sectional view showing an embodiment of the strain sensor of the blood purification apparatus according to the present invention and showing a vertical cross-sectional view of the strain sensor mounted on the air trap.
Figure 5:
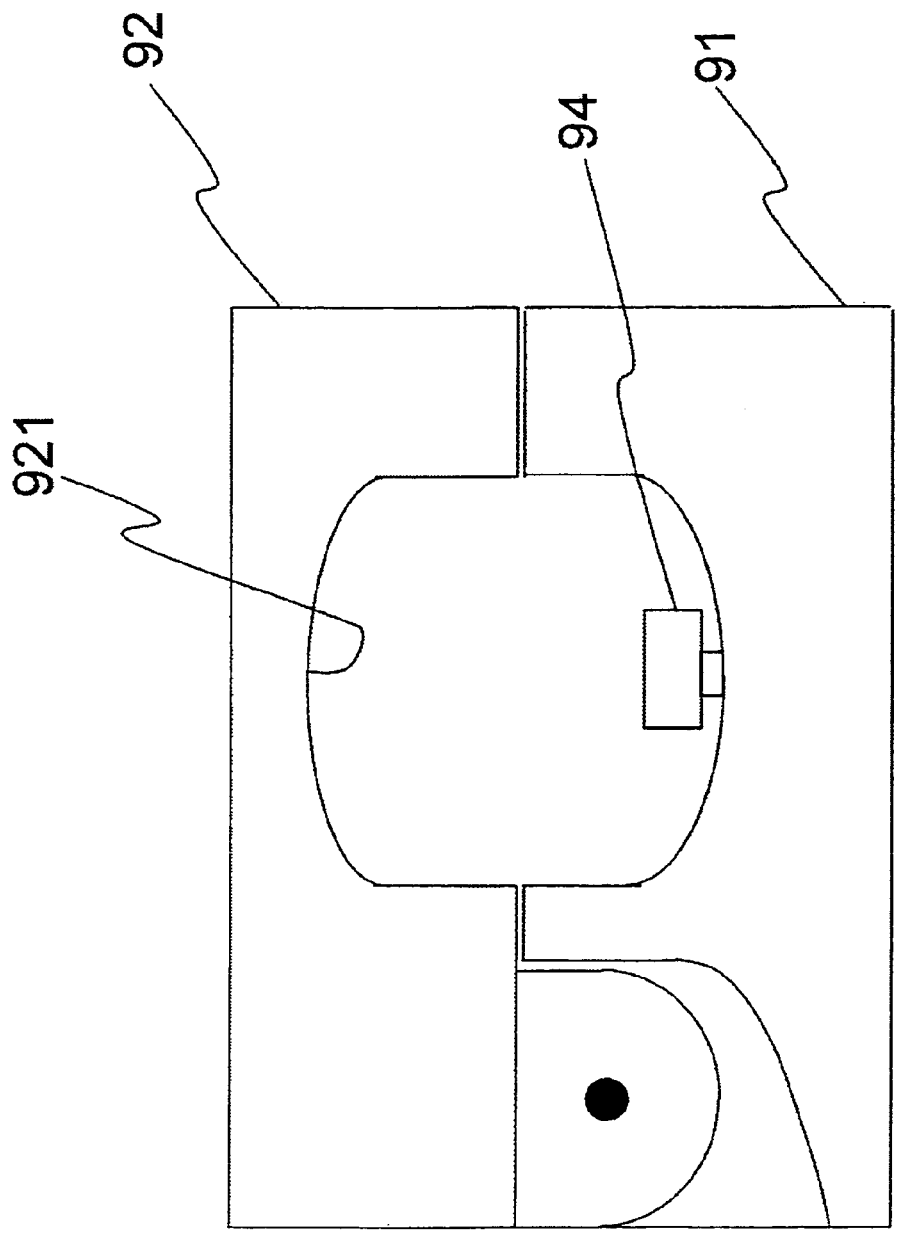
FIG. 5 is a front view of the strain sensor shown in FIG. 4.
Figure 6:
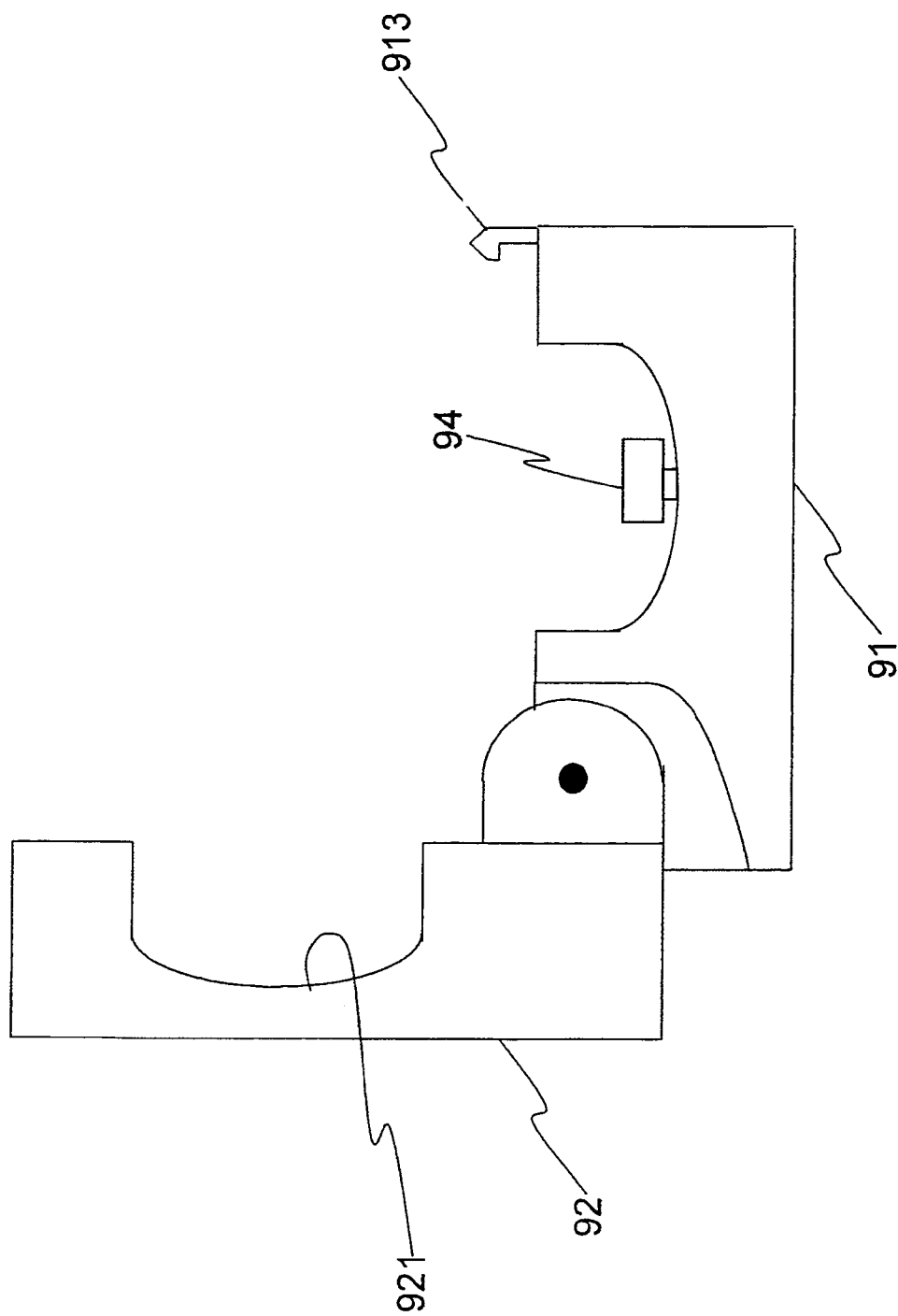
FIG. 6 is a view showing the strain sensor of FIG. 4 with its lid opened.
Figure 7:
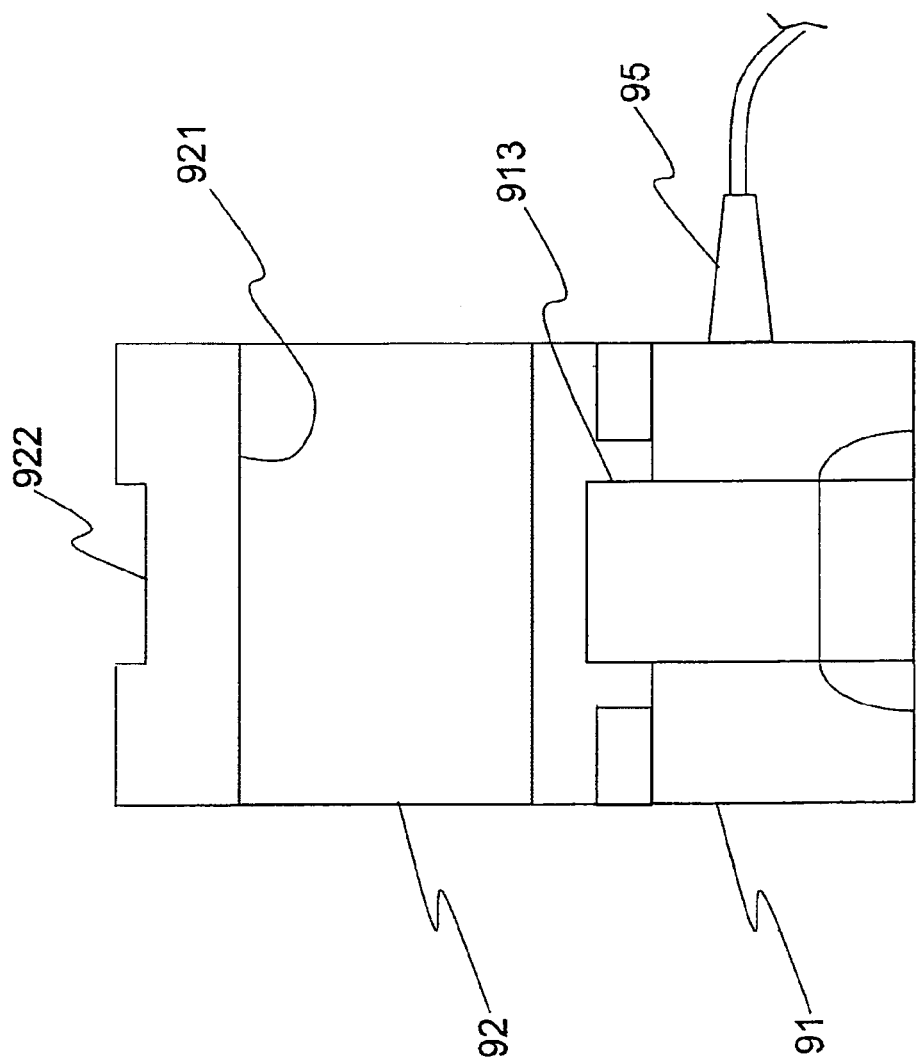
FIG. 7 is a side view of FIG. 6.

Referring now to FIG. 2, a second embodiment of the present invention will be described.

FIG. 2 is a schematic diagram of a blood purification apparatus according to the second embodiment.

The blood purification apparatus according to the second embodiment is the apparatus shown in FIG. 1, provided with a replenisher feed line 8 in the venous-side blood circuit 22, so that the replenisher is fed from a replenisher container 81 to the venous-side blood circuit 22 via the venous-side air trap 24 by the driving of a replenisher pump 82. In this blood purification apparatus, continuous venovenous hemofiltration (CVVHF) or continuous venovenous hemodiafiltration (CVVHDF) are also possible in addition to CVVHD.

Subsequently, the usage of the blood purification apparatus according to the second embodiment will be described.

When using the blood purification apparatus, prior to the treatment priming of the replenisher feed line 8 on the blood circuit 2 side and the dialysate circuit 5 side is performed. In order to conduct priming entirely at the same time, the opening-closing valve V1 of the venous-side blood circuit 22 and the opening-closing valve V2 of the priming liquid feed line 4 is opened. Then, as regards the blood circuit 2, the blood pump 3 is driven and the priming liquid (normally, saline is used) is fed from the priming liquid container 41 to the blood circuit 2 via the priming liquid feed line, for priming the arterial-side blood circuit 21, the blood purifier 1, and the venous-side blood circuit 22, and washing simultaneously. As regards the dialysate circuit 5, the dialysate pump 6 and the filtering pump 7 are driven, a dialysate is fed from the dialysate container 53 to the blood purifier 1 through the dialysate circuit 5, and the priming is conducted for the dialysate feed circuit 51, the blood purifier 1, and the drainage circuit 52. As regards the replenisher feed line, the replenisher pump 82 is driven, the replenisher is fed from the replenisher container 81 through the replenisher line 8 to the venous-side air trap 24, and the priming is conducted for the replenisher line 8 and the venous-side blood circuit 22 on the downstream side from the air trap 24.

When the priming is completed for the blood circuit 2 side and the dialysate circuit 5 side, and for the replenisher feed line 8, it is necessary to carry out calibration of the strain sensors S1, S2 and determine a straight line showing the relation between the strain and the pressure of the air traps 23, 24.

When the blood pump 3, the dialysate pump 6, and the filtering pump 7 are stopped and the opening-closing valve V1 is closed first, pressures P1, P2 measured by the strain sensors S1, S2 can be determined by using head h1, h2 between the strain sensors S1, S2 and the pressure gauge P and a pressure P3 measured by the pressure gauge P.

Therefore, the calibration can be carried out mechanically by a control unit provided in the blood purification apparatus according to the following equations 1 and 2:

$$P1 = P3 - ah1 \quad\quad 1$$

$$P2 = P3 + ah2 \quad\quad 2$$

(where a represents a constant for converting the head pressure of liquid in the circuit into a mercury pressure).

Figure 11:
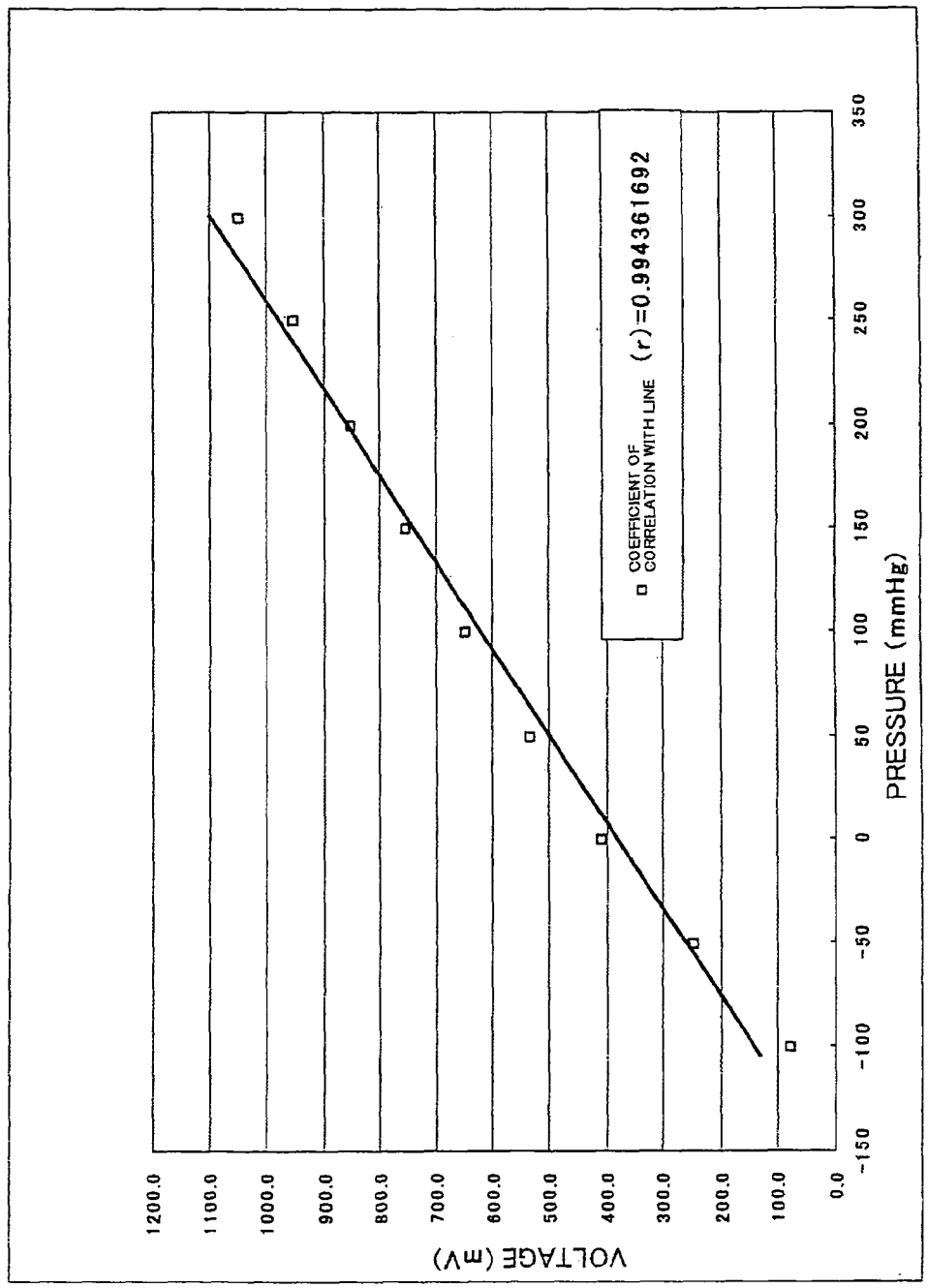
FIG. 11 is a view showing the relation between the strain of the strain sensor in an air trap and the pressure.

When the calibration of the strain sensors S1, S2 is completed, then the dialysate pump 6 and the filtering pump 7 are driven at pressure gauge P 100 mmHg and 300 mmHg, for example so that, and the strains of the air traps 23, 24 (converted into voltage by the strain sensors S1, S2) are obtained respectively. Since the voltage value (strain) and the pressure are in a linear relation as seen in FIG. 11, a straight line showing the relation between the strain (voltage) and the pressure, with the vertical axis representing the voltage value, and the lateral axis representing the pressure, can be obtained. The pressure on the blood side can be measured automatically from the strains of the air traps 23, 24 measured by the strain sensors thereafter by storing the "strain-pressure line" in the control unit provided in the blood purification apparatus.

The relation between the strain measured by the strain sensor and the internal pressure of the air trap can be obtained by measuring the strain (converted into the voltage value by the strain sensor) of the air trap when the pressure is changed in various manners, and plotting the voltage value on the vertical axis and the pressure on the lateral axis (FIG. 11). Accordingly, it is understood that the voltage value (strain) and the pressure have a linear relation, provided that the air trap has a shore A hardness of 90, an outer diameter of 20.0 mm, and an inner diameter of 17.2 mm.

Figure 8:
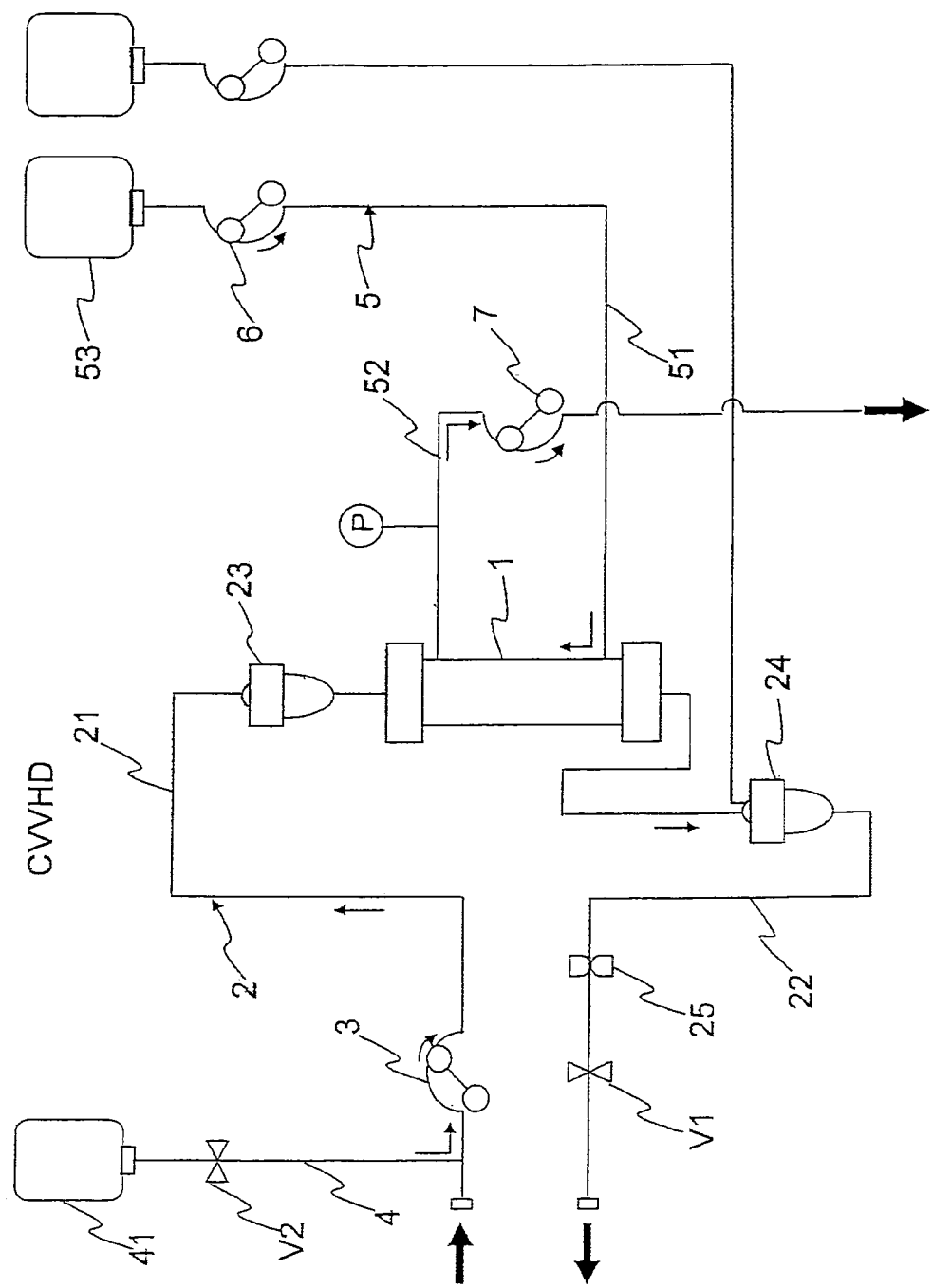
FIG. 8 is a view explaining CVVHD performed using the blood purification apparatus according to the present invention.

Subsequently, referring to FIG. 8, CVVHD will be described.

Prior to the treatment, the opening-closing valves V1 and V2 are opened, the blood pump 3, the dialysate pump 6, and the filtering pump 7 are driven, and then the priming is carried out on the blood circuit 2 side and the dialysate circuit 5 side. The blood pump 3, the dialysate pump 6 and the filtering pump 7 are stopped, the opening-closing valve V1 is closed, and then the calibration of the strain sensors S1, S2 is carried out, and a curved line representing the relation between the strains of the air traps 23, 24, and the pressure is determined.

Subsequently, after the blood pump 3, the dialysate pump 6, and the filtering pump 7 are stopped the opening-closing valve V2 closed, and the blood circuit 2 connected to the blood vessel of a patient, when the blood pump 3, the dialysate pump 6, and the filtering pump 7 are driven again the blood is fed through the arterial-side blood circuit 21 to the blood purifier 1, where the blood is purified (dialyzed), and fed back to the blood vessel of the patient through the venous-side blood circuit 22. On the other hand, the dialysate passes through the dialysate feed circuit 51 to the blood purifier 1, where it purifies the blood, and then the used dialysate is drained through the drainage line 52.

When calibration is required for the strain sensors S1, S2 during the treatment, the blood pump 3, the dialysate pump 6, and the filtering pump 7 are stopped in the same procedure as described above, and the opening-closing valve V1 is closed before carrying out the calibration. Necessity of calibration of the strain sensors S1, S2 during the treatment is determined in the following procedure by observing the pressures P1, P2 measured by the strain sensors S1, S2.

In other words, when the value of (P1-P2) increases, it means that clogging of the membrane of the blood purifier has occurred, and when the value of (P1-P2) decreases, it means that leakage has occurred in the membrane of the blood purifier. When both of the values P1 and P2 increase, it means that clogging of a needle has occurred, while when both of the values P1 and P2 decrease, disconnection of the needle has occurred. Therefore, the calibration of the strain sensors S1, S2 is necessary when any change in the values P1 and P2 other than those described above has occurred.

Figure 9:
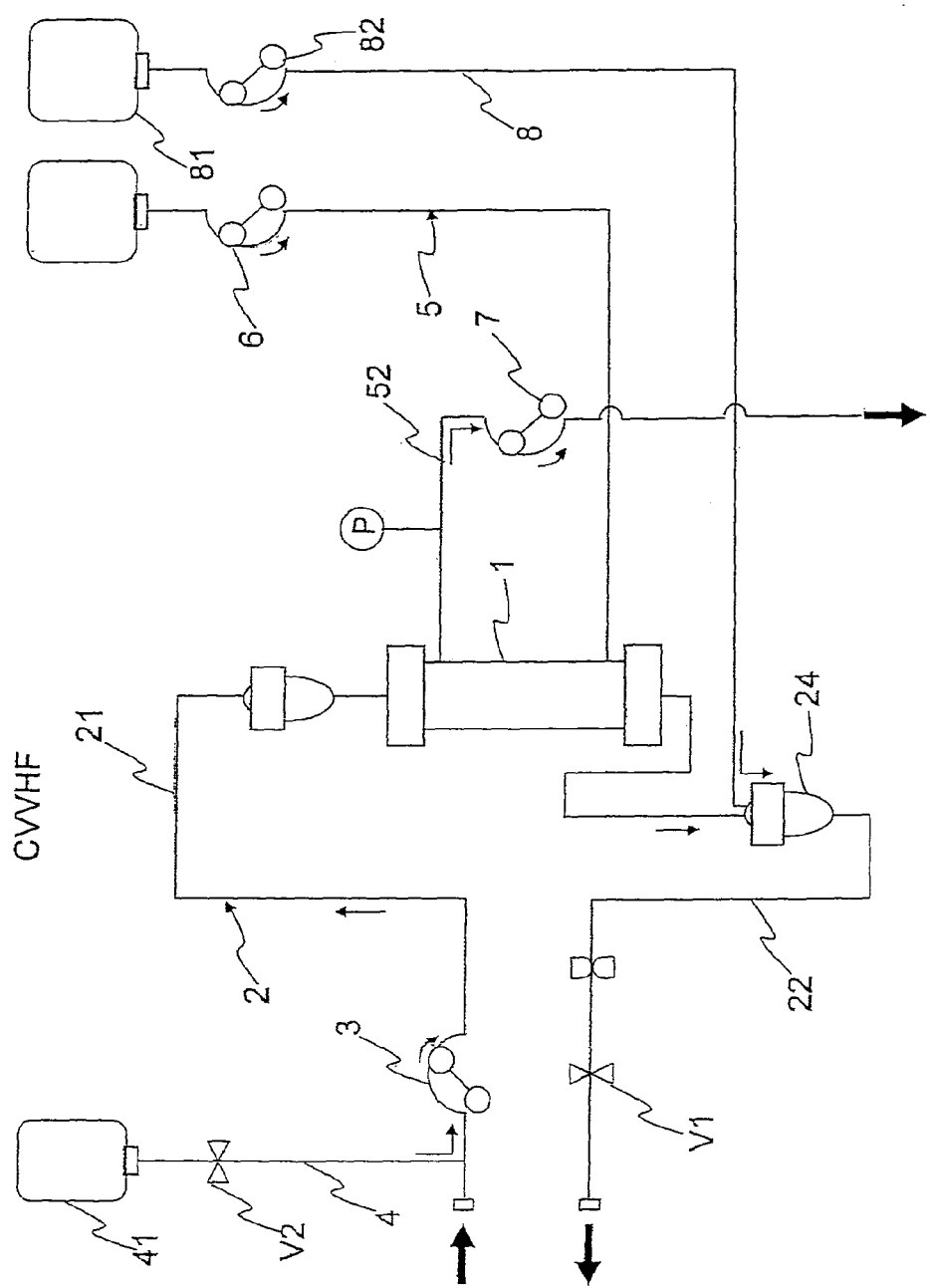
FIG. 9 is a view explaining CVVHF performed using the blood purification apparatus according to the present invention.

Referring now to FIG. 9, CVVHF will be described.

The opening-closing valves V1 and V2 of the venous-side blood circuit 22 are opened prior to the treatment, and then the blood pump 3, the dialysate pump 6, the filtering pump 7, and the replenisher pump 82 are driven to conduct priming on the blood circuit 2 side, the dialysate circuit 5 side, and the replenisher feed line 8. Then, the blood pump 3, the dialysate pump 6, and the filtering pump 7 are stopped and the opening-closing valve V1 is closed to carry out the calibration of the strain sensors S1, S2 and determine a straight line indicating the relation between the strains of the air traps 23, 24, and the pressure.

Subsequently, the blood pump 3, the dialysate pump 6, the filtering pump 7, and the replenisher pump 82 are stopped, the opening-closing valve V2 is closed, and then the blood circuit 2 is connected to the blood vessel of the patient. Subsequently, when the blood pump 3, the filtering pump 7 and the replenisher pump 82 are driven again, the blood passes through the arterial-side blood circuit 21 to the blood purifier 1, where the blood is purified (filtered) and returned to the blood vessel of the patient through the venous-side blood circuit 22. The liquid (filtered liquid) filtered from the blood is drained through the drainage line 52. On the other hand, the replenisher is supplied through the replenisher feed line 8 to the air trap 24, and fed to the blood vessel of the patient through the venous-side blood circuit 22. The method of calibration for the strain sensors S1, S2 during the treatment is the same as in CVVHD.

Figure 10:
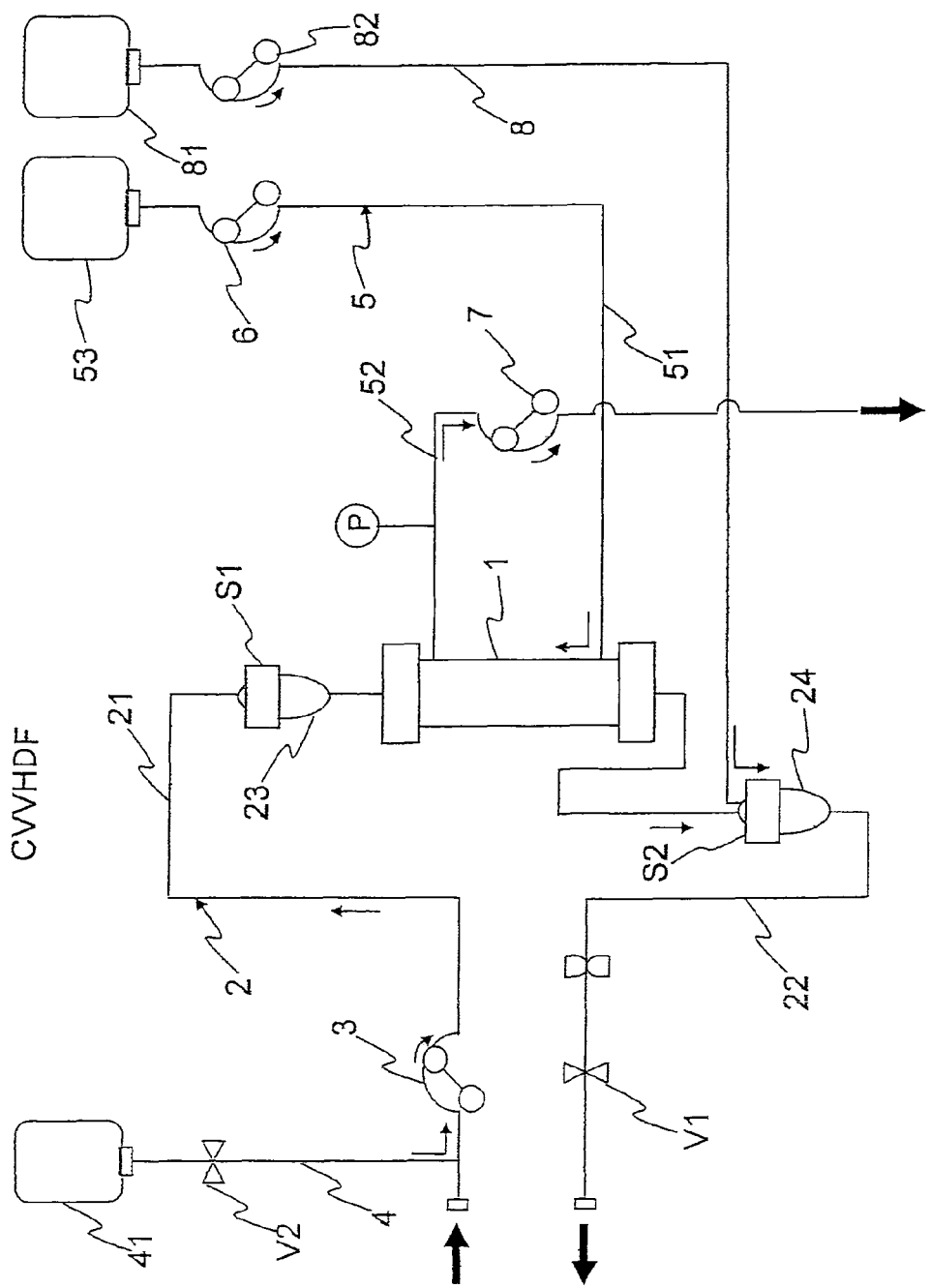
FIG. 10 is a view explaining CVVHDF performed using the blood purification apparatus according to the present invention.

Referring now to FIG. 10, CVVHDF will be described.

Prior to the treatment, the opening-closing valves V1 and V2 are opened, the blood pump 3, the dialysate pump 6, the filtering pump 7 and the replenisher pump 82 are driven, and the priming is carried out for the blood circuit 2 side, the dialysate circuit 5 side and the replenisher feed line 8. Then, the blood pump 3, the dialysate pump 6 and the filtering pump 7 are stopped, the opening-closing valve V1 is closed, and the calibration of the strain sensors S1, S2 is carried out and a straight line representing the relation between the strain of the air traps 23, 24 and the pressure is determined.

Subsequently, when the opening-closing valve V2 is closed, the blood circuit 2 is connected to the blood vessel of the patient, and then the blood pump 3, the dialysate pump 6, and the filtering pump 7 are driven, the blood is fed through the arterial-side blood circuit 21 to the blood purifier 1, where the blood is purified (filtered and dialyzed), and returned to the blood vessel of the patient through the venous-side blood circuit 22. On the other hand, the dialysate is fed to the blood purifier 1 through the dialysate feed circuit 51, where the blood is purified, and the used dialysate is drained through the drainage line 52 together with the filtered liquid from the blood. The replenisher is fed to the air trap 24 through the replenisher feed line 8 and fed to the blood vessel of the patient through the venous-side blood circuit 22. The method of calibration of the strain sensors S1, S2 during the treatment is the same as in the case of CVVHD.

INDUSTRIAL APPLICABILITY

According to the present invention, the following effects are expected. First, since the pressure in the venous-side blood circuit is determined by directly measuring the strain of a venous-side air trap by a strain sensor without providing a pressure measuring section in the blood circuit, the blood purification apparatus has no risk of generating plaque. Secondly, since the blood circuit can be configured into a simple structure and a disposable blood circuit can be manufactured at a low cost as shown, the financial burden on a patient can be reduced.

This application claims priority of Japanese patent application No. 2004-322498 filed Nov. 5, 2004, which is incorporated herein by reference.

What is claimed is:

1. A blood purification apparatus comprising:
a blood purifier and a blood circuit connected to the blood purifier and having an arterial-side blood circuit on an upstream side of the blood purifier and a venous-side blood circuit on a downstream side of the blood purifier,
a blood pump provided in the blood circuit,
a priming liquid feed line connected to the, blood circuit,
a venous-side air trap provided in the venous-side blood circuit,
an opening-closing valve provided in the venous-side blood circuit on the downstream side of the venous-side air trap,
a dialysate circuit connected to the blood purifier,
a dialysate pump and filtering pump provided in the dialysate circuit, and
a pressure gauge provided in the dialysate circuit and arranged between the dialysate pump and the filtering pump,
configured such that a strain sensor is provided on an outer wall of a body portion of the venous-side air trap, the strain sensor comprising a load sensor and a load transmitter with the load transmitter being in hermetical contact with the outer wall of the body portion of the venous-side air trap so that the strain of an outer wall of a body portion of the venous-side air trap resulting from a force exerted onto the internal surface of the venous-side air trap is sensed by the load transmitter and is transmitted to the load sensor via the load transmitter and measured, thereby measuring the pressure in the venous-side blood circuit,
configuration such that the strain sensor is calibrated by using the head between the pressure gauge and the strain sensor, and by using a pressure measured by the pressure gauge.

2. The blood purification apparatus according to claim 1, wherein an air trap is provided in the arterial-side blood circuit and a strain sensor is provided on the arterial-side air trap1 so that the pressure in the arterial-side blood circuit can be measured by measuring the strain of an outer wall of a body portion of the arterial-aide air trap by the strain sensor.

3. The blood purification apparatus according to claim 1, wherein a replenisher feed line is provided in the venous-side blood circuit.

4. The blood purification apparatus according to claim 1, wherein the strain sensor is accommodated in a housing which comprises a groove which can accommodate a body of the air trap and a load sensor compartment formed on the bottom of the groove.

5. The blood purification apparatus according to claim 4, wherein the housing is provided with means for fixing the air trap in the groove.

6. The blood purification apparatus according to claim 5, wherein the fixing means is a lid which can be locked with the housing.

7. The blood purification apparatus according to claim 2, wherein a replenisher feed line is provided in the venous-side blood circuit.

* * * * *